(12) United States Patent
Prabhu

(10) Patent No.: US 9,649,209 B2
(45) Date of Patent: *May 16, 2017

(54) HYBRID STENT AND METHOD OF MAKING

(71) Applicant: Abbott Cardiovascular Systems Inc., Santa Clara, CA (US)

(72) Inventor: Santosh Prabhu, Santa Clara, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 300 days.

This patent is subject to a terminal disclaimer.

(21) Appl. No.: 14/314,358

(22) Filed: Jun. 25, 2014

(65) Prior Publication Data

US 2014/0306378 A1    Oct. 16, 2014

Related U.S. Application Data

(60) Division of application No. 13/543,422, filed on Jul. 6, 2012, now Pat. No. 8,772,672, which is a (Continued)

(51) Int. Cl.
*A61F 2/89* (2013.01)
*A61F 2/82* (2013.01)
(Continued)

(52) U.S. Cl.
CPC .......... *A61F 2/89* (2013.01); *A61F 2/04* (2013.01); *A61F 2/82* (2013.01); *A61F 2/91* (2013.01); *A61F 2/915* (2013.01); *A61L 31/022* (2013.01); *A61L 31/10* (2013.01); *A61L 31/16* (2013.01); *A61L 31/18* (2013.01); *B23K 26/38* (2013.01); *B23K 26/402* (2013.01); *B29C 41/08* (2013.01);
(Continued)

(58) Field of Classification Search
CPC .......... Y10T 428/139; A61F 2002/072; A61F 2002/91558; A61F 2230/0013; A61F 2230/0054; A61F 2250/0063; A61F 2250/0067; A61F 2/07; A61F 2/91; A61F 2/82; A61F 2/915; A61F 2/852; A61F 2/89; B29L 2031/7534
See application file for complete search history.

(56) References Cited

U.S. PATENT DOCUMENTS 5,756,553 A * 5/1998 Iguchi .................... A61L 27/54
424/425
5,837,313 A * 11/1998 Ding ......................... A61F 2/82
427/2.21

(Continued)

FOREIGN PATENT DOCUMENTS

IE    WO 9934855 A1 *  7/1999  ........ A61M 25/0009

Primary Examiner — Catherine A Simone
(74) Attorney, Agent, or Firm — Fulwider Patton LLP

(57) ABSTRACT

A stent is formed by encasing or encapsulating metallic rings in an inner polymeric layer and an outer polymeric layer. At least one polymer link connects adjacent metallic rings. The stent is drug loaded with one or more therapeutic agent or drug, for example, to reduce the likelihood of the development of restenosis in the coronary arteries. The inner and outer polymeric materials can be of the same polymer or different polymer to achieve different results, such as enhancing flexibility and providing a stent that is visible under MRI, computer tomography and x-ray fluoroscopy.

21 Claims, 5 Drawing Sheets

Related U.S. Application Data continuation of application No. 13/094,617, filed on Apr. 26, 2011, now Pat. No. 8,242,409, which is a division of application No. 11/832,091, filed on Aug. 1, 2007, now Pat. No. 7,959,999, which is a continuation of application No. 10/113,358, filed on Apr. 1, 2002, now Pat. No. 7,691,461.

(51) Int. Cl.

| | | |
|---|---|---|
| A61F 2/91 | (2013.01) | |
| A61F 2/915 | (2013.01) | |
| A61L 31/02 | (2006.01) | |
| A61L 31/10 | (2006.01) | |
| A61L 31/18 | (2006.01) | |
| B29C 41/08 | (2006.01) | |
| B29C 41/14 | (2006.01) | |
| B29C 41/20 | (2006.01) | |
| B29C 41/22 | (2006.01) | |
| B23K 26/38 | (2014.01) | |
| B29C 65/16 | (2006.01) | |
| B29C 65/68 | (2006.01) | |
| B23K 26/402 | (2014.01) | |
| A61F 2/04 | (2013.01) | |
| A61L 31/16 | (2006.01) | |
| A61F 2/852 | (2013.01) | |
| A61F 2/07 | (2013.01) | |
| B29L 31/00 | (2006.01) | |
| B23K 103/00 | (2006.01) | |

(52) U.S. Cl.
CPC .............. *B29C 41/14* (2013.01); *B29C 41/20* (2013.01); *B29C 41/22* (2013.01); *B29C 65/16* (2013.01); *B29C 65/68* (2013.01); *A61F 2/07* (2013.01); *A61F 2/852* (2013.01); *A61F 2002/072* (2013.01); *A61F 2002/91558* (2013.01); *A61F 2210/0076* (2013.01); *A61F 2230/0013* (2013.01); *A61F 2230/0054* (2013.01); *A61F 2230/0069* (2013.01); *A61F 2250/0032* (2013.01); *A61F 2250/0063* (2013.01); *A61F 2250/0067* (2013.01); *B23K 2203/42* (2015.10); *B29L 2031/7534* (2013.01); *Y10T 29/49906* (2015.01); *Y10T 428/139* (2015.01); *Y10T 428/1393* (2015.01)

(56) References Cited

U.S. PATENT DOCUMENTS

| | | | |
|---|---|---|---|
| 5,897,911 A | 4/1999 | Loeffler | |
| 5,948,018 A | 9/1999 | Dereume et al. | |
| 6,139,573 A * | 10/2000 | Sogard | A61F 2/07 623/1.13 |
| 6,398,803 B1 | 6/2002 | Layne et al. | |
| 6,517,888 B1 | 2/2003 | Weber | |
| 6,520,986 B2 | 2/2003 | Martin et al. | |
| 7,504,125 B1 | 3/2009 | Pacetti et al. | |
| 7,691,461 B1 * | 4/2010 | Prabhu | A61F 2/82 428/36.9 |
| 7,959,999 B2 * | 6/2011 | Prabhu | A61F 2/82 428/36.9 |
| 2001/0001317 A1 | 5/2001 | Duerig et al. | |
| 2003/0125799 A1 | 7/2003 | Limon | |
| 2004/0199242 A1 | 10/2004 | Hong et al. | |

\* cited by examiner

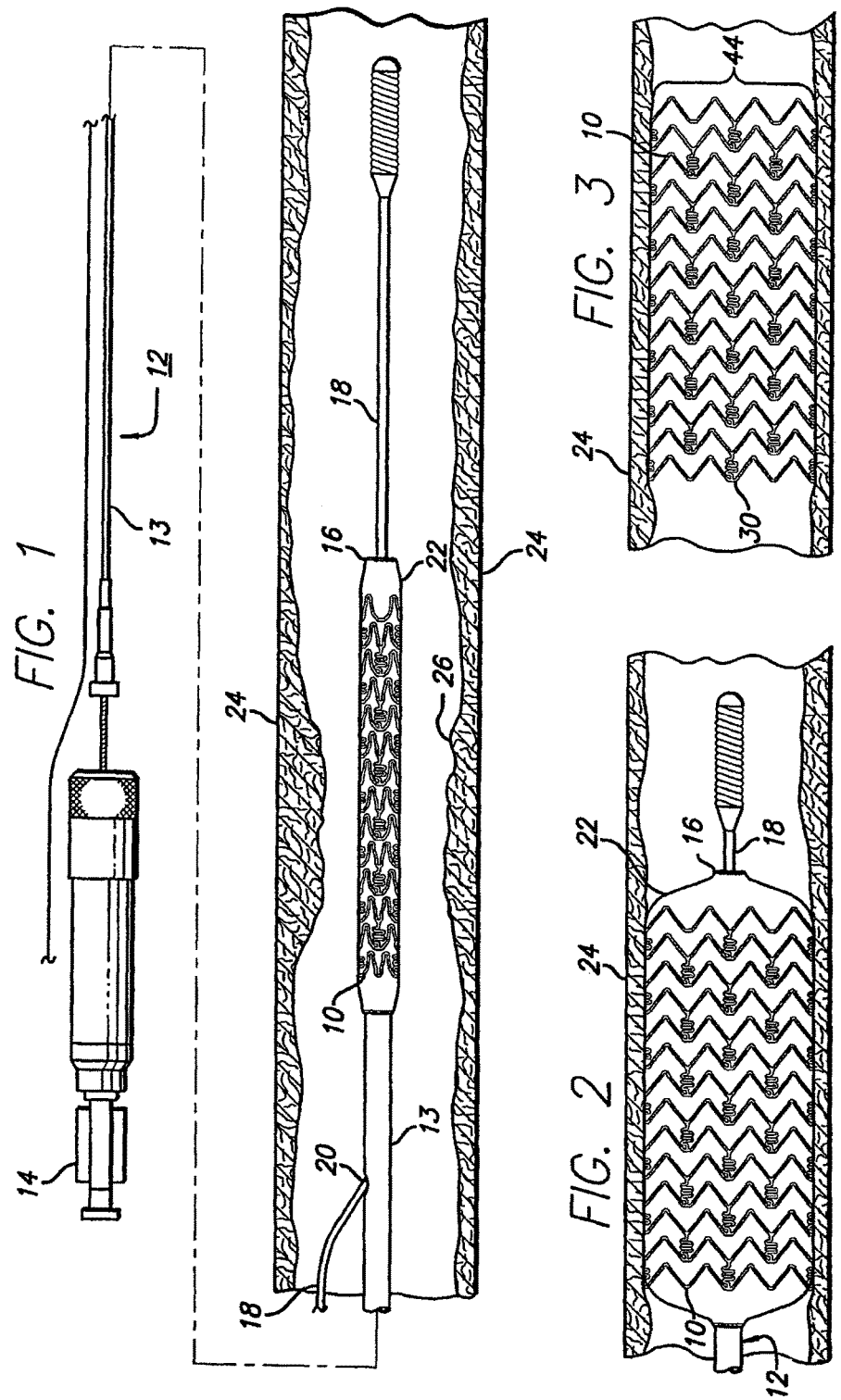

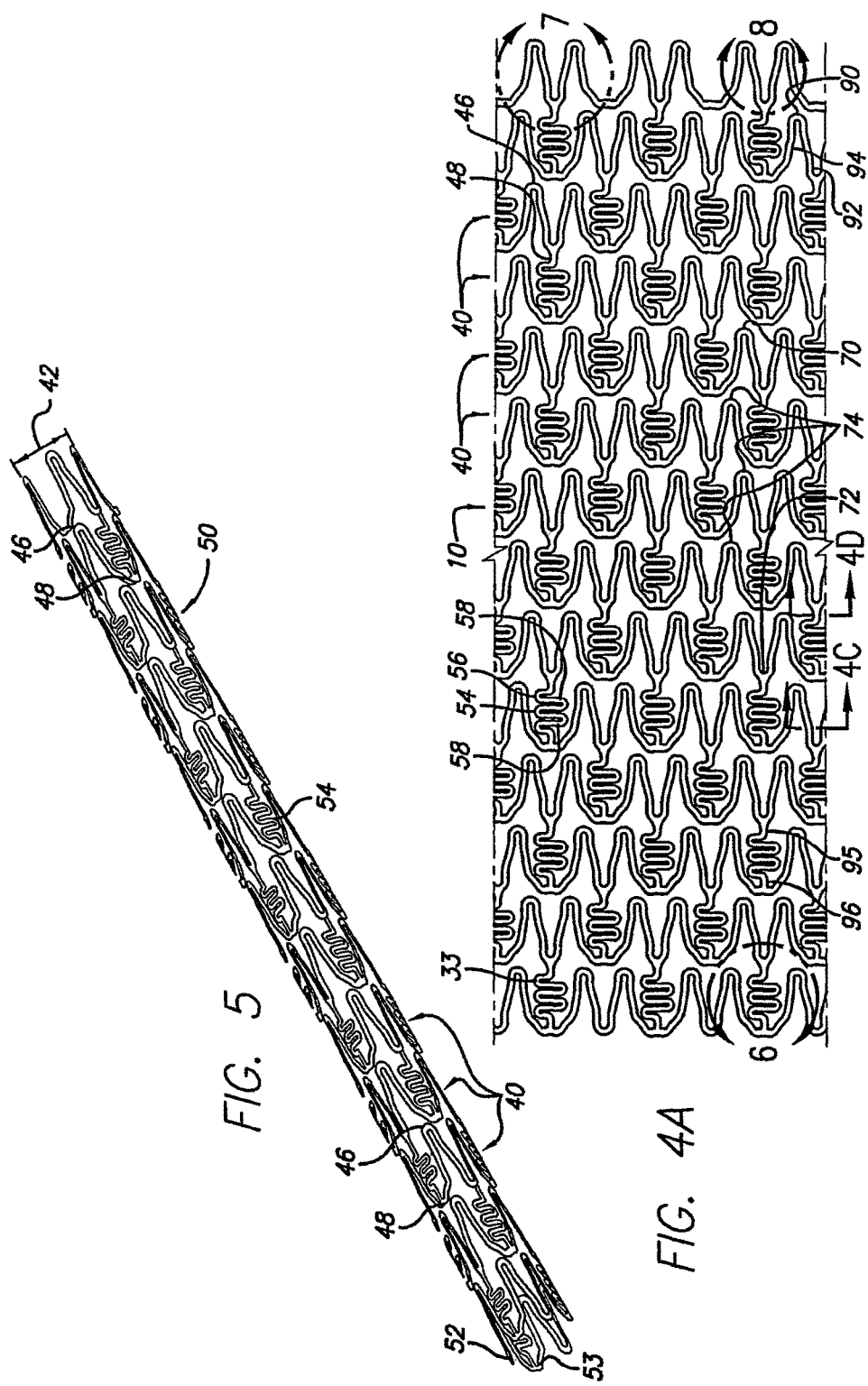

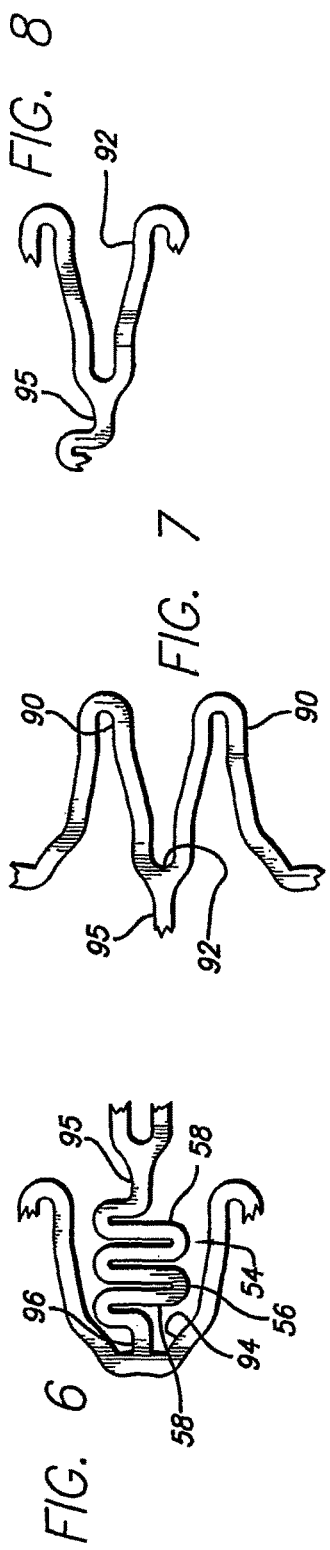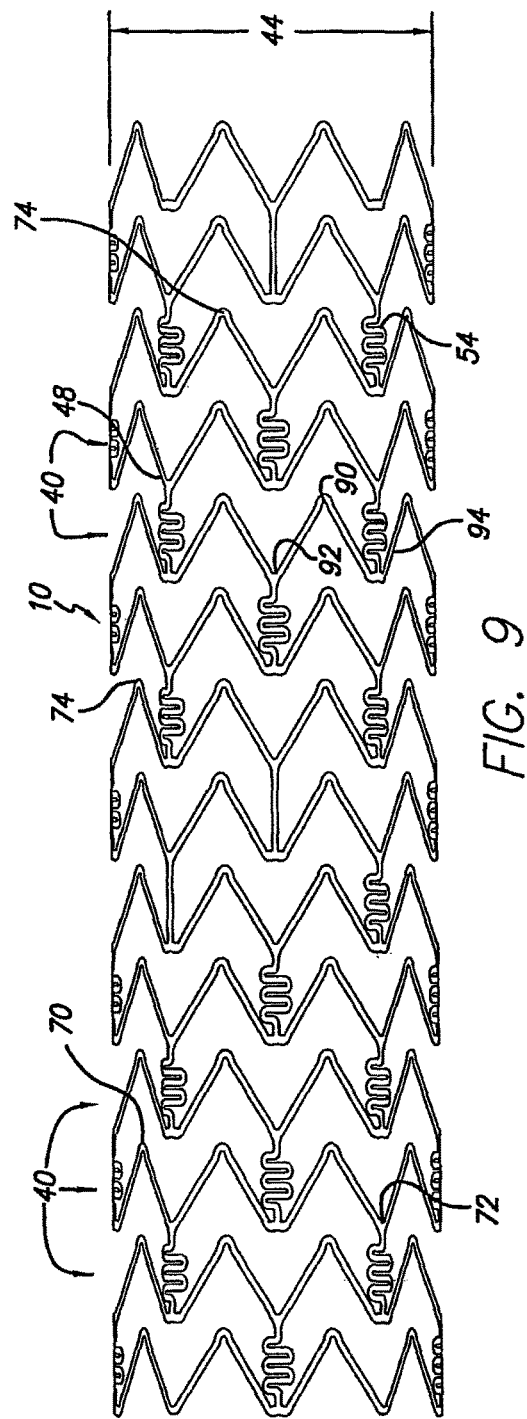

HYBRID STENT AND METHOD OF MAKING

CROSS-REFERENCES TO RELATED APPLICATIONS

This application is a division of U.S. Ser. No. 13/543,422 which is a continuation of U.S. Ser. No. 13/094,617 filed Apr. 26, 2011, now U.S. Pat. No. 8,242,409, issued Aug. 14, 2012 which is a division of U.S. Ser. No. 11/832,091, filed Aug. 1, 2007, now U.S. Pat. No. 7,959,999, issued Jun. 14, 2011, which is a continuation of U.S. Ser. No. 10/113,358, filed Apr. 1, 2002, now U.S. Pat. No. 7,691,461, issued Apr. 6, 2010, the contents of which are incorporated by reference herein in their entirety.

BACKGROUND

This invention relates to endoprosthesis devices, generally called stents, and more particularly, to achieving desired visibility of such devices under magnetic resonance imaging (MRI), computer tomography, and fluoroscopy.

Stents are generally thin walled tubular-shaped devices composed of complex patterns of interconnecting struts which function to hold open a segment of a blood vessel or other body lumen such as a coronary artery. They also are suitable for supporting a dissected arterial lining or intimal flap that can occlude a vessel lumen. At present, there are numerous commercial stents being marketed throughout the world. These devices are typically implanted by use of a catheter which is inserted at an easily accessible location and then advanced through the vasculature to the deployment site. The stent is initially maintained in a radially compressed or collapsed state to enable it to be maneuvered through the lumen. Once in position, the stent is deployed. In the case of balloon expandable stents, deployment is achieved by inflation of a balloon about which the stent is carried on a stent-delivery catheter.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of localized portions of the stent structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, there is a requirement that a stent be radiopaque or fluoroscopically visible under x-rays. Accurate stent placement requires real time visualization to allow the cardiologist or interventional radiologist to track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. This is typically accomplished by the use of radiopaque materials in the construction of a stent, which allows for its direct visualization. The most common materials used to fabricate stents are stainless steel and nickel-titanium alloys, both of which are radiopaque. This factor, in combination with the radial wall thickness of about 0.002 to 0.009 inch of most stent patterns, renders stents produced from these materials sufficiently radiopaque to be optimally visualized with x-ray based fluoroscopy procedures. Although both materials are generally regarded as being bio-compatible, some recent concerns have arisen regarding the long term biocompatibility of stainless steel. Over time, nickel, a constituent element of most stainless steels, tends to leach from a stainless steel stent. In addition, the chromium oxide layer present on the surface of stainless steel stents to prevent corrosion may have a tendency to degrade during long term use within the body.

Alternative, non-toxic, high density metals, such as cobalt-chromium, tantalum, iridium, platinum, gold, and the like, have been used in prior art stents. However, these alloys can sometimes either be excessively radiopaque or may lack sufficient strength for recoil, radial strength requirements, and long-term use in a dynamic vascular setting. Stents constructed of highly radiopaque materials appear overly bright when viewed under a fluoroscope. This tends to overwhelm the image of the tissue surrounding the stent and obscures visualization of the stent lumen. Due to the lack of an appropriately radiopaque material, simply constructing a stent wholly out of a single material has heretofore not resulted in a stent with the optimal combination of mechanical properties and radiopacity. Thus, the art has moved in the direction of combining different materials to produce a mechanically sound, biocompatible and fluoroscopically visible stent. A number of such approaches have been developed. Typically such methods have focused on increasing the radiopacity or fluoroscopic visibility of stainless steel and nickel-titanium alloy stents.

One means frequently described for increasing fluoroscopic visibility is the physical attachment of radiopaque markers to the stent. Conventional radiopaque markers, however, have a number of limitations. Upon attachment to a stent, such markers may project from the surface of the stent, thereby comprising a departure from the ideal profile of the stent. Depending on their specific location, the marker may either project inwardly to disrupt blood flow or outwardly to traumatize the walls of the blood vessel. Additionally, galvanic corrosion may result from the contact of two disparate metals, i.e., the metal used in the construction of the stent and the radiopaque metal of the marker. Such corrosion could eventually cause the marker to separate from the stent which may be problematic should the marker be swept downstream within a vessel. Discrete stent markers cannot show the entire outline of the stent which is a preferred method to determine the optimal expansion of a stent over its entire length.

The radiopacity of stents has also been increased by plating or coating selected portions thereof with radiopaque material. However, a number of disadvantages are associated with this approach as well. When the stent is expanded certain portions undergo substantial deformation, creating a risk that cracks may form in the plating or coating causing portions of the plating to separate from the underlying substrate. This has the potential for creating jagged edges that may inflict physical trauma on the lumen wall tissue or cause turbulence in the blood flowing past the stent, thereby inducing thrombogenesis. Moreover, once the underlying structural material becomes exposed to an electrolytic solution such as blood, interfaces between the two disparate metals become subject to galvanic corrosion. Over time, galvanic corrosion may also lead to separation of the plated material from the underlying substrate.

X-ray based fluoroscopy is the current preferred modality for imaging stents during an intervention and for diagnostic assessment. However, in addition to the potential disadvantages stated above, other drawbacks may exist. Exposure to ionizing radiation and nephrotoxic iodinated contrast agents are intrinsic to the technique, as well as the need to wear leaded personal protective equipment. Alternatively, magnetic resonance imaging (MRI), produced by complex interactions of magnetic and radio-frequency fields, does not suffer from these drawbacks and is actively being pursued to image stents in a diagnostic mode and, in the future, to guide stent based interventions. MRI has gained an increasing role in the diagnosis and assessment of human pathology. In patients undergoing MRI, there are numerous devices which are poorly seen, if they are visible at all, on the MR image artifact. The location and course of these implanted devices is usually of great clinical importance to assure their proper function and avoid complications that malposition can cause.

Due to their small size, current metal stents are sometimes difficult to see in fluoroscopy as they attenuate the x-ray beam very little. This is particularly true in very large, obese patients being imaged in lower end grade imaging systems. In MRI, the problem is that ferromagnetic and metallic based stents are difficult to see as they can create a large imaging artifact (a region of signal void or diminishment, which can extend beyond the stent boundaries). A plastic medical device, namely a polymeric stent, is particularly better for MRI as it is non-ferromagnetic and non-metallic. Indeed, a polymeric stent produces substantially no artifact at all. The signal used in most conventionally available MRI comes from the nuclear magnetic resonance of hydrogen nuclei. Polymers contain hydrogen atoms but these nuclei resonate at a frequency which is shifted from the water hydrogen signal from which the image is mainly derived. Moreover, the emitted RF signal from, polymers is quite broad. Under MRI, polymers appear as a region of signal void that is the same size as the device and therefore, more clinically accurate. Unfortunately, this creates a situation analogous to fluoroscopy with a stent that is difficult to visualize. A solution to imaging a polymeric stent under MRI is to add a substance to the polymer to change its magnetic susceptibility. These materials are well known to those skilled in the art and consist of paramagnetic or ferromagnetic compounds, particles and fillers. By the choice of agent, and its concentration in the polymer, the size of the susceptibility artifact can be tuned.

Fluoroscopy generates a two-dimensional projection image of what are three-dimensional structures. This requires multiple views to appraise complex vasculature. Another imaging modality, which has the potential to supplant fluoroscopy and become important in the diagnostic imaging of stents, is magnetic resonance imaging (MRI). One advantage of MRI is that it is a tomographic imaging technique that generates a 3-D data set of the imaged tissue. Consequently, the data set can be manipulated to show different imaging planes and slice thicknesses. This permits high quality transverse, coronal and sagittal images to be obtained directly. MRI has greater soft tissue contrast and tissue discrimination than computed tomography (CT) or other x-ray based imaging modalities, such as angiography. As another advantage, MRI also does not use ionizing radiation and does not require catheterization to image the vasculature.

The technique of MRI encompasses the detection of certain atomic nuclei (those possessing magnetic dipole moments) utilizing magnetic fields and radio-frequency (RF) radiation. It is similar in some respects to x-ray computed tomography in providing a cross-sectional display of the body organ anatomy, only with excellent resolution of soft tissue detail. In its current use, the images constitute a distribution map of protons, and their properties, in organs and tissues. However, unlike x-ray computer tomography, MRI does not use ionizing radiation. The fundamental lack of any known hazard associated with the level of the magnetic and radio-frequency fields that are employed renders it possible to make repeated scans. Additionally, any scan plane can readily be selected, including transverse, coronal, and sagittal sections. MRI is, therefore, a safe non-invasive technique for medical imaging.

The hydrogen atom, having a nucleus consisting of a single unpaired proton, has one of the strongest magnetic dipole moments of nuclei found in biological tissues. Since hydrogen occurs in both water and lipids, it is abundant in the human body. Therefore, MRI is most commonly used to produce images based upon the distribution density of protons and/or the relaxation times of protons in organs and tissues. The majority of the signal in MRI comes from water. Tissues vary in their water content, but for angiography, blood is the relevant tissue. Blood is approximately 93% water. This translates into a proton concentration of 103 moles/liter. However, MRI can image tissues with a lower water content. For example, grey matter and bone are 71% and 12% water respectively. It must be noted that MRI can image proton concentrations much lower than those of blood or grey matter. Image resolution is determined by the signal to noise (S/N) ratio. Faster acquisition of data or longer acquisition times both increase the signal to noise ratio.

MRI is presently used for diagnostic applications, but interventional MRI is an active area of research. For devices to be seen under MRI, they must be MRI compatible. In the context of a diagnostic or interventional procedure, this refers to the ability to accurately image a stent. MRI imaging schemes for devices are divided into two categories, active and passive. Active imaging requires some sort of electrical circuit on, or electrical connection to, the device. This presently is not an easily implemented solution for small, free-standing devices such as stents. The passive imaging scheme that applies readily to metal stents is based on the stent material's magnetic susceptibility and electrical conductivity.

Because stents are constructed of electrically conductive materials, they suffer from a Faraday Cage effect when used with MRI's. Generically, a Faraday Cage is a box, cage, or array of electrically conductive material intended to shield its contents from electromagnetic radiation. The effectiveness of a Faraday Cage depends on the wave length of the radiation, the size of the mesh in the cage, the conductivity of the cage material, its thickness, and other variables. Stents do act as Faraday Cages in that they screen the stent lumen from the incident RF pulses of the MRI scanner. This prevents the proton spins of water molecules in the stent lumen from being flipped or excited. Consequently, the desired signal from the stent lumen is reduced by this diminution in excitation. Furthermore, the stent Faraday Cage likely impedes the escape of whatever signal is generated in the lumen. The stent's high magnetic susceptibility, however, perturbs the magnetic field in the vicinity of the implant. This alters the resonance condition of protons in the vicinity, thus leading to intravoxel dephasing with an attendant loss of signal. The net result with current metallic stents, most of which are stainless steel, is a signal void in the MRI images. Other metallic stents, such as those made from Nitinol, also have considerable signal loss in the stent lumen due to a combination of Faraday Cage and magnetic susceptibility effects.

At this time, MRI is being used to non-invasively image many regions of the vasculature. The comprehensive cardiac MRI exam has demonstrated clinical utility in the areas of overall cardiac function, myocardial wall motion, and myocardial perfusion. It may become the standard diagnostic tool for heart disease. With these advances in imaging technologies, a stent that can be meaningfully imaged by MRI in an optimal manner would be advantageous. A non-metallic stent obviously solves the imaging problem. Metals, however, are the preferred material as they make strong, low profile stents possible. Unfortunately, most metal stents, particularly of stainless steel, obliterate MRI images of the anatomy in their vicinity and obscure the stent lumen in the image. By reducing the amount of metal in the stent, or by making the cells larger, or by having fewer cells, the Faraday Cage effect may be reduced. The RF radiation used in MRI has a wavelength of 2 to 35 meters depending on the scanner and environment of the stent. Therefore, the cell sizes of stents are already much smaller than the RF wavelength. Increasing the stent cell size would work only primarily by decreasing the amount of metal. This solution is limited by the need for stents to have adequate radial strength and scaffolding.

However, MRI has the potential to supplant, and potentially substitute for fluoroscopy in the future. Stents which are more compatible with this imaging modality, or which have a dual functionality, may have a clinical performance benefit. Both the future of stent materials, and the imaging modalities used to visualize them are areas of intense research due to the clinical value and large market for stents, particularly coronary stents. Although metal alloy stents currently dominate the marketplace, polymer stents have potential advantages in the areas of hemocompatibility, biodegradability, and drug delivery.

What is needed therefore is a stent that overcomes the shortcomings inherent in previously known devices. Preferably, such a stent would be formed of a hybrid material, possess the required mechanical characteristics, and also be readily visible using MRI, computer tomography, and x-ray based fluoroscopy procedures.

SUMMARY OF THE INVENTION

The present invention is directed to a stent that overcomes the shortcomings of previously known devices by embodying a polymeric material combined with a metallic material to improve visibility under MRI, computer tomography and fluoroscopy.

In one embodiment of the stent of the present invention, metallic rings are positioned between an outer layer of a first polymeric material and an inner layer of a second polymeric material. In other words, the metallic rings are sandwiched in between the first and second polymeric materials. The rings are connected by links which are formed by the first and second polymeric materials. The metallic rings generally are visible under fluoroscopy while the polymeric material provides good visibility using MRI.

The first and second polymeric materials can be taken from a group of polymeric materials which includes polyetheretherketone (PEEK), ethyl vinyl alcohol (EVOH), polyetherketone, polymethylmethacrylate, polycarbonate, polyphenylenesulfide, polyphenylene, polyvinylfluoride, polyvinylidene fluoride, polypropylene, polyethylene, poly (vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate, polyimides and polyetherimide. Other polymeric materials that could be used to form the inner or outer polymeric material include ePTFE, polyurethanes, polyetherurethanes, polyesterurethanes, silicone, thermoplastic elastomer (e.g. C-flex), polyether-amide thermoplastic elastomer (e.g., Pebax), fluoroelastomers, fluorosilicone elastomer, styrene-butadiene-styrene rubber, styrene-isoprene-styrene rubber, polybutadiene, polyisoprene, neoprene, ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, butadiene and isoprene (e.g., Kraton) and polyester thermoplastic elastomer (e.g., Hytrel) and a di-block co-polymer of PET and caprolactone. For strength, the polymer may further contain reinforcements such as glass fiber, carbon fiber, Spectra™, or Kevlar™.

The metallic rings of each of the embodiments of the present invention are formed from materials that are visible under fluoroscopy, such as metallic alloys. The metallic alloys can be self-expanding or balloon expandable and can include stainless steel, titanium, nickel-titanium, tantalum, cobalt-chromium, and the like.

In another embodiment, in order to provide higher visibility under fluoroscopy, the polymeric materials are compounded with an appropriate radiopacifier such as the powder of barium sulfate, bismuth subcarbonate, bismuth trioxide, bismuth oxychloride, tungsten, tantalum, iridium, gold, or other dense metal. To define a biodegradable structure, the polymeric materials are compounded with a biodegradable radiopacifier that renders it visible under fluoroscopy and can be safely released in the body. Such radiopacifiers include particles of an iodinated contrast agent and bismuth salts.

The first and second polymeric materials also can be formed of self-expanding polymers including shape memory polymers such as oligo (e-caprolactone), dimethylacrelate, and n-butyl acrylate.

Each embodiment of the present invention also can include a therapeutic drug or therapeutic agent associated with the first and second polymeric materials. For example, one or more therapeutic drugs can be loaded into either or both of the first and second polymeric materials to prevent or reduce the likelihood of restenosis or to otherwise treat the vessel or artery.

The hybrid stent of the present invention can be made in several ways. In one embodiment, the metallic rings are cut by a laser using conventional laser cutting procedures. The rings are then mounted on an inner polymeric tube which has been premounted on a teflon mandrel. After the rings have been mounted and positioned on the inner polymeric tube, an outer polymeric tube is mounted over the metallic rings and the inner polymeric tube. A shrink tubing is then mounted over the outer polymeric tube and it is subjected to laser bonding so that the shrink tubing contracts and applies pressure to the outer polymeric tube causing it to compress against the metallic rings and the inner polymeric tube. Further, heat from the laser causes the outer and inner polymeric tubes to partially melt and fuse together. An appropriate bonding agent can be used to help adhere the inner and outer tubes together. The shrink tubing and the supporting teflon mandrel are removed and the stent pattern is then formed by a laser to remove unwanted portions of the polymer material, so that a pattern of metallic rings encased by the polymer material are attached to each other by polymeric links as previously disclosed.

In another embodiment to make the hybrid stent of the present invention, a mandrel is first dip coated into a polymer which corresponds to the inner polymeric material. The metallic rings, which previously were laser cut from a tube, are mounted on the inner polymer material and positioned to form the stent pattern. The outer layer or outer polymer material is deposited over the metal rings either by spray coating or by dip coating the outer polymeric material over the rings and the inner polymeric material. The mandrel is removed and the unwanted portions of the polymers can be machined by using laser cutting as previously described.

It is to be recognized that the stent of the present invention can be self-expanding or balloon-expanded. Moreover, the present invention can be modified to be used in other body lumens including highly tortuous and distal vasculature.

These and other features and advantages of the present invention will become apparent from the following detailed description, which when taken in conjunction with the accompanying drawings, illustrate by way of example the principles of the invention.

BRIEF DESCRIPTION OF THE DRAWINGS

FIG. 1 is an elevation view, partially in section, of the balloon-expandable hybrid stent of the invention mounted on a rapid-exchange delivery catheter and positioned within an artery.

FIG. 2 is an elevation view, partially in section, similar to that shown in FIG. 1, wherein the hybrid stent is expanded within the artery so that the stent embeds within the arterial wall.

FIG. 3 is an elevation view, partially in section, showing the expanded hybrid stent implanted within the artery after withdrawal of the rapid-exchange delivery catheter.

FIG. 4A is a plan view of a flattened stent which illustrates the pattern of the hybrid stent shown in FIGS. 1-3.

FIG. 5 is a perspective view of a pre-expanded balloon expandable hybrid stent depicting the cylindrical wall defined by the cylindrical rings.

FIG. 6 is an enlarged sectional view of FIG. 4 depicting a W-shaped portion of a cylindrical ring.

FIG. 7 is an enlarged sectional view of FIG. 4 depicting several U-shaped or undulating peaks of a cylindrical ring.

FIG. 8 is an enlarged sectional view of FIG. 4 depicting a Y-shaped portion of the cylindrical ring.

FIG. 9 is a plan view of the hybrid stent in a flattened and expanded condition.

DETAILED DESCRIPTION OF THE PREFERRED EMBODIMENTS

Figure 4B:
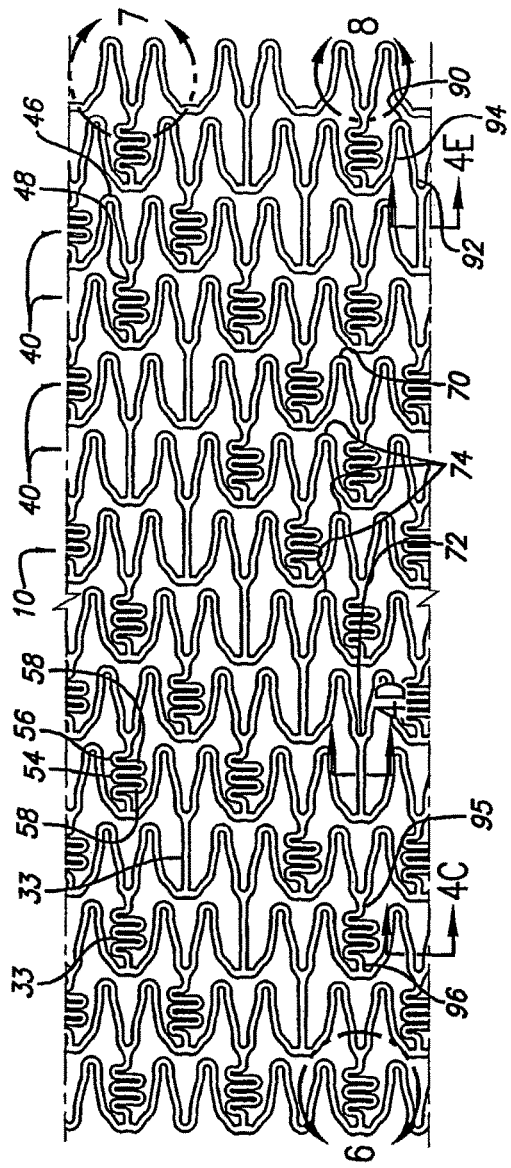
FIG. 4B is a plan view of a flattened stent which illustrates the hybrid stent with some straight polymeric links.

The hybrid stent of the present invention combines the features and advantages of metallic stents with those of polymeric stents so that the combined hybrid stent provides the required structural support for a vessel such as a coronary artery, yet is visible under any of MRI, computer tomography or x-ray fluoroscopy. In general, metallic rings are aligned along a stent longitudinal axis and an outer layer of a first polymeric material covers the outer surface of the metallic rings, and an inner layer of a second polymeric material covers the inner surface of the metallic rings. At least one link connects adjacent metallic rings whereby the links are formed by the inner and outer polymeric materials. Virtually any stent pattern, of the many known stent patterns, can be used to form the hybrid stent of the present invention. Thus, while certain embodiments of the hybrid stent are described herein, they are for exemplary purposes only, and are not meant to be limiting.

Turning to the drawings, FIG. 1 depicts a hybrid stent 10 mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient=s vascular system by advancing over a guide wire by any of the well known methods of an over-the-wire system (not shown) or a well known rapid exchange catheter system, such as the one shown in FIG. 1.

Catheter assembly 12, as depicted in FIG. 1, includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit particular applications. The stent is mounted on the expandable member 22 (a catheter balloon) and is crimped tightly thereon so that the stent and expandable member present a low profile diameter for delivery through the arteries.

As shown in FIG. 1, a partial cross-section of an artery 24 contains a small amount of plaque that has been previously treated by an angioplasty or other repair procedure. Stent 10 is used to repair a diseased or damaged arterial wall or a dissection or flap, which are commonly found in the coronary arteries and other blood vessels.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty or other procedure (e.g., atherectomy) in order to open and remodel the vessel and the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is supporting the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

Due to the formation of the metallic portion of the hybrid stent 10 from a tube, the straight and undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the cylindrical rings are closely spaced at regular intervals to provide uniform support for the wall of the artery, and consequently are well adapted to tack up and hold in place small flaps or dissections in the wall of the artery.

Turning to FIG. 4A, one embodiment of the hybrid stent 10 is shown as flat sheet, so that the pattern can be clearly viewed, even though the stent is not in this form when in use. The stent is typically formed from a tubular member, although it can be formed from a flat sheet and rolled into a cylindrical configuration or by other known means.

The hybrid stent 10 of the present invention, as shown in FIGS. 4-9, includes a metallic ring material 30 that provides structural support and vessel wall coverage. The metallic ring material is sandwiched through an outer polymeric material 31 and inner polymeric material 32 so that the metallic ring material is completely encased in the two polymeric layers or materials. Portions of the polymeric materials are removed to form links 33 which then connect the metallic ring material. The overall structure thus includes metallic rings connected by links, whereby the metallic rings are formed of a metal alloy sandwiched between an outer polymeric material and an inner polymeric material and the links which are formed of the outer polymeric material and the inner polymeric material. As shown, for example, in FIGS. 4C and 4D, the metallic ring material is sandwiched between an outer polymeric material and an inner polymeric material (FIG. 4C) while the cross-sectional view of the links (FIG. 4D) shows an outer polymeric material and an inner polymeric material bonded together. The polymeric links will increase the longitudinal and flexural flexibility of the stent which facilitates delivery of the stent through tortuous lumens, such as the coronary arteries or vessels in the brain. Further, the polymeric links will permit the stent to conform with arterial walls after expansion. The number of metallic rings and the number of connecting links can vary depending upon the application, and since the polymeric links are typically more flexible than prior art metallic links, more of the polymeric links connecting each ring are available, which provides more support for the vessel wall. Additionally, since the polymeric links are highly flexible, comparatively more metallic rings can be used than with conventional all metallic stents without compromising the overall flexibility of the stent. By increasing the number of polymeric links and the number of metallic rings, the amount of scaffolding or wall coverage provided by the stent is greatly increased, thereby reducing instances of plaque prolapse.

In one embodiment, the inner polymeric material 32 is made from polyetheretherketone (PEEK). PEEK offers a higher flexibility compared to most metallic alloys, for example, PEEK has a module of elasticity (E) of 4 GPa compared to stainless steel which has an E of 200 GPa. Further, PEEK has excellent radiographic qualities which include elimination of imaging artifacts and scatter generated from metallic implants which would prevent a complete visualization of tissue when using conventional imaging techniques such as x-ray, computer tomography or MRI. Since PEEK is MRI compatable, MRI technologies can be used to scan patients implanted with the hybrid stent 10 of the present invention having an inner polymeric material made from PEEK. Further, PEEK can be modified to enhance its radiopacity. For example, PEEK-Optima J (made by Invibio Biomaterial Solutions, Greenville, S.C.) has been modified to be radiopaque under fluoroscopy and is suitable for implant applications. The outer polymeric material 31 can be a polymer such as ethyl benyl alcohol (EVOH); available commercially as EVAL™, EVAL Company of America, Lisle, Ill.), which again provides flexibility that is comparable to PEEK, and is substantially more flexible than stainless steel, for example. The first and second polymeric materials can be taken from a group of polymeric materials which includes polyetheretherketone (PEEK), ethyl vinyl alcohol (EVOH), polyetherketone, polymethylmethacrylate, polycarbonate, polyphenylenesulfide, polyphenylene, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate, polyimides and polyetherimide. Other polymeric materials that could be used to form the inner or outer polymeric material include ePTFE, polyurethanes, polyetherurethanes, polyesterurethanes, silicone, thermoplastic elastomer (e.g. C-flex), polyether-amide thermoplastic elastomer (e.g., Pebax), fluoroelastomers, fluorosilicone elastomer, styrene-butadiene-styrene rubber, styrene-isoprene-styrene rubber, polybutadiene, polyisoprene, neoprene, ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, butadiene and isoprene (e.g., Kraton) and polyester thermoplastic elastomer (e.g., Hytrel) and a di-block co-polymer of PET and caprolactone. For strength, the polymer may further contain reinforcements such as glass fiber, carbon fiber, Spectra™, or Kevlar™.

In one embodiment, the outer polymeric material 31 and/or the inner polymeric material 32 are loaded with a therapeutic agent or drug for treating the artery or vessel in which the hybrid stent 10 is implanted. As an example, an anti-restenotic drug can be loaded into the PEEK or EVOH of the outer polymeric material or the inner polymeric material to reduce the likelihood of the development of restenosis of a coronary artery. In another embodiment, as shown in FIG. 4E, a cavity 34 is formed between the outer polymeric material 31 and the inner polymeric material 32 for containing a therapeutic drug 35. The drug would elute through the polymeric material at a controlled rate to treat the artery or vessel in which the stent is implanted. In the embodiment shown in FIG. 4E, cavity 34 is positioned between the first polymeric material and the second polymeric material in the polymeric link 33. One or more links can be formed to create the cavity and then loaded with a therapeutic agent or drug in order to prevent the development of restenosis, or to treat the artery or vessel for other conditions, such as to reduce clot formation.

Examples of therapeutic agents or drugs that are suitable for use with the outer and inner polymeric materials 31,32 include rapamycin, actinomycin D (ActD), or derivatives and analogs thereof ActD is manufactured by Sigma-Aldrich, 1001 West Saint Paul Avenue, Milwaukee Wis. 53233, or COSMEGEN, available from Merck. Synonyms of actinopmycin D include dactinomycin, actinomycin IV, actinomycin I1, actinomycin X1, and actinomycin C1. Examples of agents include other antiproliferative substances as well as antineoplastic, antiinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein, IIb/IIIa platelet membrane receptor antagonist, recombinant hirudin, thrombin inhibitor (available from Biogen), and 7E-3B™ (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

The metallic ring material 30 of the present invention can include alloys such as stainless steel, titanium, tantalum, nickel-titanium, cobalt-chromium, tungsten, and similar metallic alloys that are biocompatible and that are generally known for use as intravascular stents.

The hybrid stent 10 of the present invention can be incorporated in a wide range of stent patterns that are widely known and currently available. Many of the currently available stent patterns include some combination of cylindrical rings that have an undulating shape that is crimpable onto the balloon portion of a catheter and expandable for implanting in an artery or a vessel. Typically, the rings are connected by connecting members or links with both the rings and links being formed of the same metal, such as stainless steel, titanium, or cobalt-chromium. Thus, the hybrid stent of the present invention can be used to make any of the following commercially available stents that go by the trade names ACS Multi-Link™ family of stents made by Advanced Cardiovascular Systems, Inc., Santa Clara, Calif.; the BX Velocity Stent™ made by Cordis, a Johnson & Johnson company, Warren, N.J.; the AVE S670™ and S7™ stents made by AVE, a division of Medtronic Corporation, Minneapolis, Minn.; and the NIR™ and the Express™ stents made by Medinol and distributed in the United States by Boston Scientific, Corp., Natick, Mass. As a further example, an ACS Multi-Link™ PENTA stent is further described herein for purposes of illustration to demonstrate its conformability to the hybrid stent 10 of the present invention.

In keeping with the invention, as shown in FIGS. 4-9, one embodiment of the hybrid stent 10 is made up of cylindrical rings 40 which extend circumferentially around the stent when it is in a tubular form. The stent has a delivery diameter 42 as shown in FIG. 5, and an implanted diameter 44 as shown in FIG. 3. Each cylindrical ring 40 has a cylindrical ring proximal end 46 and a cylindrical ring distal end 48. Typically, since the stent is laser cut from a tube, there are no discreet parts such as the described cylindrical rings. However, it is beneficial for identification of various parts to refer to the cylindrical rings and other parts of the stent.

Each cylindrical ring 40 defines a cylindrical plane 50 which is a plane defined by the proximal and distal ends 46, 48 and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

Undulating link 54 is positioned within cylindrical plane 50 such that the undulating links connect one cylindrical ring to an adjacent cylindrical ring and provide overall longitudinal flexibility to the stent due to their unique construction. The flexibility of undulating links derives in part from bends 56 connected to straight portions 58 wherein the straight portions are substantially perpendicular to the longitudinal axis of the stent. Thus, as the stent is being delivered through a tortuous vessel, such as a coronary artery, the bends 56 and straight portions 58 of the undulating links will permit the stent to flex in the longitudinal direction which substantially enhances delivery of the stent to the target site. The number of bends and straight portions can be increased or decreased from that shown, to achieve differing flexibility constructions. With the straight portions being substantially perpendicular to the stent longitudinal axis, the undulating link acts like a hinge to provide flexibility.

Figure 4E:
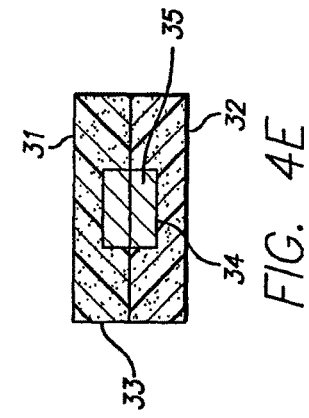
FIG. 4E is a cross-sectional view taken along lines 4E-4E depicting a polymer link having a cavity containing a therapeutic drug or agent.
Figure 4D:
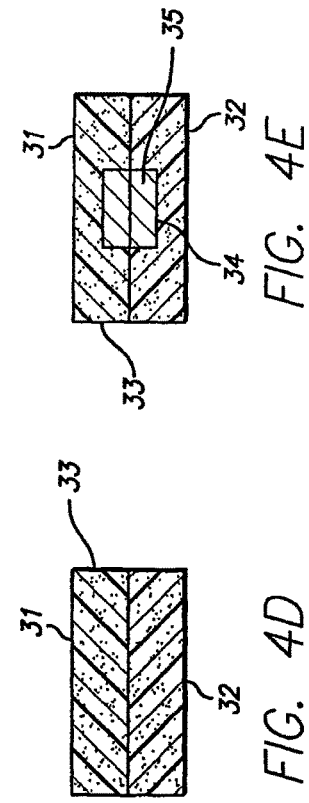
FIG. 4D is a cross-sectional view taken along lines 4D-4D depicting a polymer link.
Figure 4C:
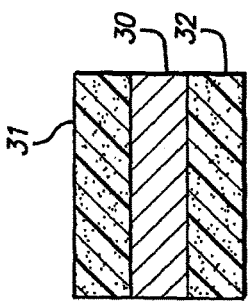
FIG. 4C is a cross-sectional view taken along lines 4C-4C depicting the hybrid strut in one of the stent rings.

Referring to FIGS. 4A, 4B and 5, the stent 10 can be described more particularly as having a plurality of peaks 70 and valleys 72. Although the stent is not divided into separate elements, for ease of discussion references to peaks and valleys is appropriate. The number of peaks and valleys, sometimes referred to as crowns, can vary in number for each ring, depending upon the application. Thus, for example, if the stent is to be implanted in a coronary artery, a lesser number of peaks and valleys (or crowns) are required than if the stent is implanted in a peripheral artery, which has a larger diameter than a coronary artery. As can be seen in FIGS. 4A and 4B, peaks 70 are substantially in phase when looking at every other cylindrical ring 40. The in-phase relationship is identified by reference number 74. It may be desirable under certain circumstances to position peaks 70 so that they are in phase in every cylindrical ring (not shown). As shown in FIG. 4A, the peaks are circumferentially offset from the valleys and from the undulating link 54. Positioning the peaks, valleys, and undulating links in this manner provides a stent having uniform expansion capabilities, high radial strength, a high degree of flexibility, and sufficient wall coverage to support the vessel.

Referring to FIGS. 6-9, the stent can be described as having U-shaped portions 90, Y-shaped portions 92, and W-shaped portions 94. Again, while the cylindrical rings are generally laser cut from a tube and the stent typically has no discreet parts, for ease of identification the stent of the invention also can be referred to as having U-, Y-, and W-shaped portions. The U-shaped portions have no supporting structure attached thereto. The Y-shaped portions, at their base, or apex, have arm 95 extending therefrom and attached to undulating link 54. The W portion has at its base or curve portion arm 96 which attaches at the other end of the undulating link. The length of the arms attaching the links to the rings can vary. Importantly, the arms should be sized in conjunction with the undulating link. Preferably, undulating link 54 is contained within W-shaped portion 94, which should be wide enough to accommodate the undulating link when the stent is crimped so that no portion of the undulating link and the W-portion overlap. Preferably, the undulating link and the W-shaped portion are in the same cylindrical plane 50 as defined by the cylindrical outer wall surface 52 and the cylindrical inner wall surface 53. FIG. 9 shows one embodiment of the hybrid stent 10 in a flattened configuration and expanded. Again, the stent normally is not in this configuration (flattened and expanded) and shown for illustration purposes to better understand the invention.

One embodiment of the hybrid stent 10 of the present invention includes a superelastic material in the metallic rings and/or the polymeric links. The term "superelastic" refers to an isothermal transformation, more specifically stress inducing a martensitic phase from an austenitic phase. Alloys having superelastic properties generally have at least two phases: a martensitic phase, which has a relatively low tensile strength and which is stable at relatively low temperatures, and an austenitic phase, which has a relatively high tensile strength and which is stable at temperatures higher than the martensitic phase. The austenitic phase also typically has better corrosion properties. Superelastic characteristics generally allow the metal stent to be deformed by collapsing and deforming the stent and creating stress which causes the metal to change to the martensitic phase. The stent is restrained in the deformed condition to facilitate the insertion into a patient's body, with such deformation causing the phase transformation. Once within the body lumen, the restraint on the stent is removed, thereby reducing the stress therein so that the superelastic stent can return towards original undeformed shape by the transformation back to the austenitic phase. A basic discussion of this phenomenon can be found in Wayman and Deuring, "An Introduction to Martensite and Shape Memory," which appears in *Engineering Aspects Of Shape Memory Alloys*, Deuring et al. editors (Butterworth-Heinemann Ltd. 1990, Great Britain.)

In this embodiment, the cylindrical ring material 30 of the hybrid stent 10 are formed from a superelastic material such as NiTi and undergo an isothermal transformation when stressed. The stent is first compressed to a delivery diameter, thereby creating stress in the NiTi alloy so that the NiTi is in a martensitic state having relatively low tensile strength. While still in the martensitic phase, the stent is mounted onto a catheter by known methods.

When stress is applied to a specimen of a metal such as nitinol exhibiting superelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase. As the phase transformation progresses, the alloy undergoes significant increases in strain with little or no corresponding increases in stress. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensite specimen will elastically recover and transform back to the austenitic phase. The reduction in stress first causes a decrease in strain. As stress reduction reaches the level at which the martensitic phase transforms back into the austenitic phase, the stress level in the specimen will remain essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity.

The prior art makes reference to the use of metal alloys having superelastic characteristics in medical devices which are intended to be inserted or otherwise used within a patient's body. See, for example, U.S. Pat. No. 4,665,905 (Jervis) and U.S. Pat. No. 4,925,445 (Sakamoto et al.), which are incorporated by reference herein in their entirety.

Figure 10:
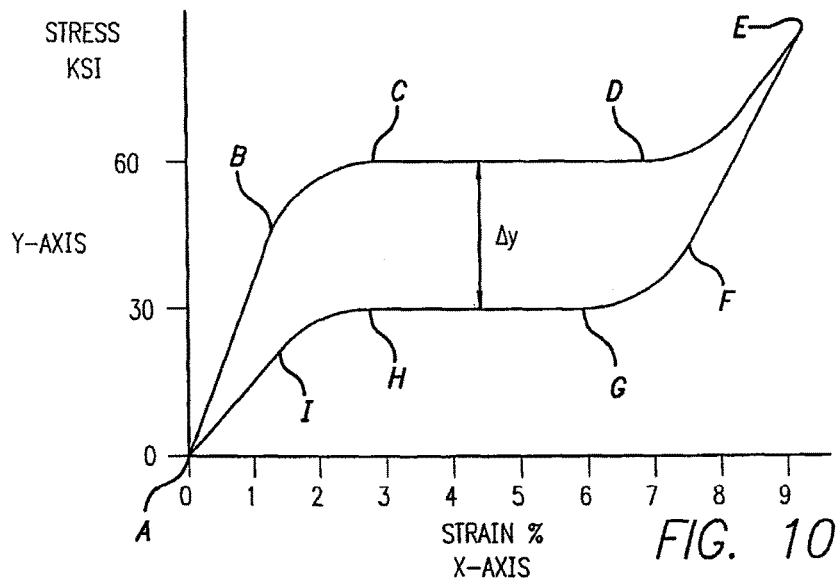
FIG. 10 is a typical stress-strain curve for a superelastic material.

FIG. 10 illustrates an example of a stress-strain relationship of an alloy specimen, the cylindrical rings having superelastic properties as would be exhibited upon tensile testing of the specimen. The relationship is plotted on x-y axis, with the x axis representing strain and the y axis representing stress. For ease of illustration, the x-y axes are labeled with typical pseudoelastic nitinol stress from 0 to 60 ksi and strain from 0 to 9 percent, respectively.

Looking at the plot itself in FIG. 10, the line from point A to point B represents the elastic deformation of the specimen. After point B the strain or deformation is no longer proportional to the applied stress and it is in the region between point B and point C that the stress-induced transformation of the austenitic phase to the martensitic phase begins to occur. There also can be an intermediate phase, called the rhombohedral phase, depending upon the composition of the alloy. At point C moving toward point D, the material enters a region of relatively constant stress with significant deformation or strain. This constant or plateau region is known as the loading stress, since it represents the behavior of the material as it encounters continuous increasing strain. It is in this plateau region CD that the transformation from austenite to martensite occurs.

At point D the transformation to the martensitic phase due to the application of stress to the specimen is substantially complete. Beyond point D the martensitic phase begins to deform, elastically at first, but, beyond point E, the deformation is plastic or permanent.

When the stress applied to the superelastic metal is removed, the material behavior follows the curve from point E to point F. Within the E to F region, the martensite recovers its original shape, provided that there was no permanent deformation to the martensitic structure. At point F in the recovery process, the metal begins to transform from the stress-induced, unstable, martensitic phase back to the more stable austenitic phase.

In the region from point G to point H, which is also an essentially constant or plateau stress region, the phase transformation from martensite back to austenite takes place. This constant or plateau region GH is known as the unloading stress. The line from point I to the starting point A represents the elastic recovery of the metal to its original shape.

Binary nickel-titanium alloys that exhibit superelasticity have an unusual stress-strain relationship as just described and as plotted in the curve of FIG. 10. As emphasized above, the superelastic curve is characterized by regions of nearly constant stress upon loading, identified above as loading plateau stress CD and unloading plateau stress GH. Naturally, the loading plateau stress CD is always larger than the unloading plateau stress GH. The loading plateau stress represents the period during which martensite is being stress-induced in favor of the original austenitic crystalline structure. As the load is removed, the stress-induced martensite transforms back into austenite along the unloading plateau stress part of the curve. The difference in stress between the stress at loading CD and unloading stress GH defines the hysteresis of the system. This is identified as $\Delta y$ of the curve in FIG. 10.

The present invention seeks to minimize the hysteresis of the superelastic material used for the self-expanding rings of the hybrid stent. The rings are designed to perform various mechanical functions within a lumen, all of which are based upon the lower unloading plateau stress GH. Unloading plateau stress GH represents the behavior of the nitinol material when the stent is deployed.

On the other hand, the higher loading plateau stress CD establishes the mechanical resistance the cylindrical rings exert against the delivery system, and specifically delivery sheath or restraint. It represents the stress exerted by the end-rings when they are loaded into a restraint. The greater the difference between the two plateaus CD and GH is (the hysteresis), the stronger the delivery system must be to accommodate any given level of stent performance.

Conversely, reducing the difference or $\Delta y$ between the two plateaus CD and GH results in smaller hysteresis. The smaller the hysteresis is, the smaller and lower profile the delivery system has to be to accommodate any given level of stent performance. Furthermore, the present invention delivery system can be smaller and constructed to a smaller profile due to the lower loading plateau stress CD, while maintaining a high hoop strength of the deployed, expanded stent represented by plateau stress GH.

The superelastic alloy is preferably formed from a composition consisting essentially of about 30 to about 52 percent titanium and the balance nickel and up to 10 percent of one or more additional ternary alloying elements. Such ternary alloying elements may be selected from the group consisting of palladium, platinum chromium, iron, cobalt, vanadium, manganese, boron, copper, aluminum, tungsten, or zirconium. In particular, the ternary element may optionally be up to 3 percent each of iron, cobalt, platinum, palladium, and chromium, and up to about 10 percent copper and vanadium. As used herein, all references to percent composition are atomic percent unless otherwise noted. Platinum is the preferred ternary element at 7.5 atomic percent.

In another embodiment, a NiTi cylindrical ring with SME (shape memory effect) is heat-treated at approximately 500E C. The stent is mechanically deformed into a first, smaller diameter for mounting on a catheter delivery system that includes an expandable balloon and inflation lumen. After the stent has been expanded by the balloon and deployed against arterial wall, 45E C heat is applied causing the cylindrical rings to return to their fully expanded larger diameter and to be in contact with the arterial wall of the artery. The application of 45E C of heat is compatible with most applications in the human body, but it is not to be limited to this temperature, as higher or lower temperatures are contemplated without departing from the invention. The 45E C temperature can be achieved in a conventional manner well known in the art, such as by warm saline injected into the delivery catheter and balloon.

In the embodiment in which the cylindrical ring material 30 is formed of a superelastic or shape memory effect metal alloy, such as NiTi, one or both of the polymers also can be formed of a shape memory polymer. Various shape memory polymers for biomedical applications can include oligo (e-caprolactone), dimethacrylate and n-butyl acrylate. Both of these shape memory polymers are monomeric compounds which, when combined, generate a family of polymers that exhibit excellent memory characteristics. The oligo (e-caprolactone) dimethacrylate furnishes the crystalisable switching segment (which is characteristic of shape memory materials changing from one phase to another) that determines both the temporary and the permanent shape of the polymer. By analogy, the temporary shape is similar to the martensitic phase of a metallic NiTi material, while the permanent shape of the polymer is similar to the austentic phase of the NiTi alloy. By varying the amount of the comonomer, n-butyl acrylate, in the polymer compound, the cross-link density can be varied. This allows the mechanical strength and the transition temperature of the polymers to be tailored over a wide range, which can be coordinated with the NiTi alloy to provide the required shape memory characteristics of the overall stent having both metallic rings and polymer links.

Figure 11:
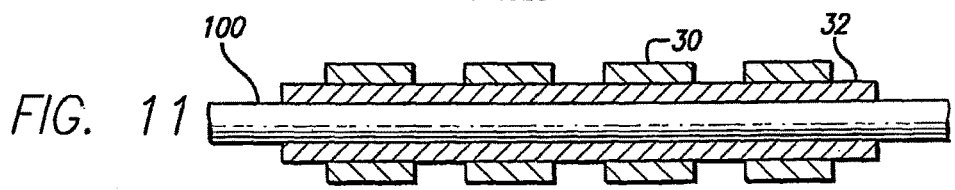
FIG. 11 is a longitudinal cross-sectional view depicting the metallic rings and polymer materials being formed on a mandrel.
Figure 12:
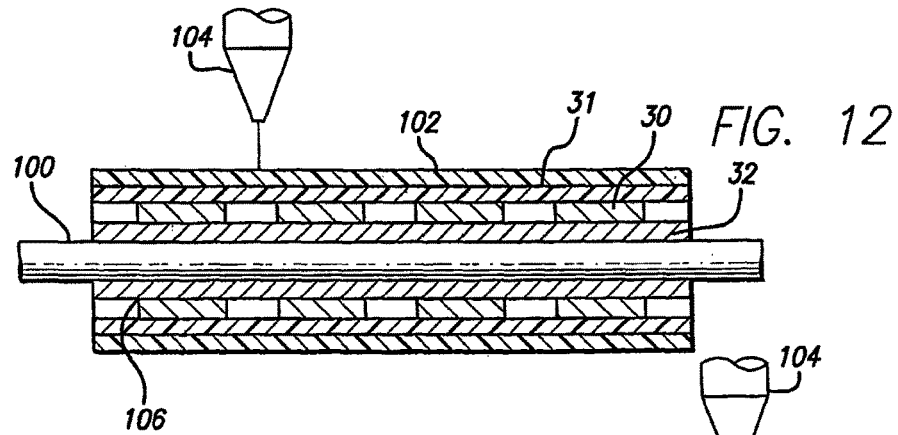
FIG. 12 is a longitudinal cross-sectional view depicting the metallic rings and polymer materials being formed on a mandrel and the unwanted portions being removed by a laser.
Figure 13:
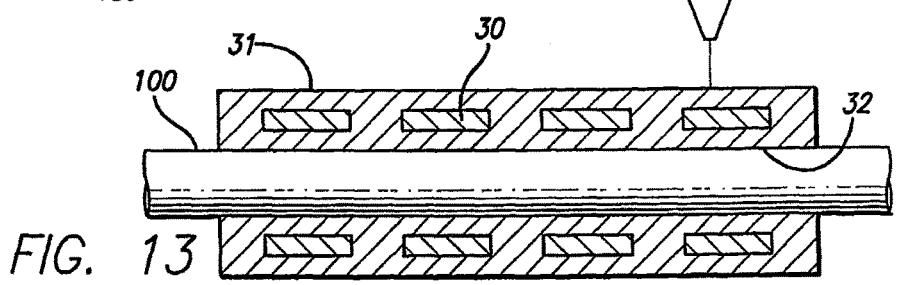
FIG. 13 is a longitudinal cross-sectional view depicting the metallic rings and polymer materials being formed on a mandrel and the unwanted portions being removed by a laser.

The hybrid stent of the present invention can be manufactured in many ways. In one embodiment, as shown in FIGS. 11-13, the metallic ring material 30 is sandwiched between or encased within outer polymeric material 31 and inner polymeric material 32. In keeping with the method of making the hybrid stent, in one embodiment, the metallic ring material 30 is cut from a tube in a conventional manner by a laser cutting procedure. One such method of laser cutting metallic rings and stent patterns in general is described in U.S. Pat. No. 5,759,192 to Saunders, which is incorporated by reference herein. The inner polymeric material 32 is mounted on a mandrel 100 so that it is a tight fit, and the metallic ring material is thereafter positioned over the inner polymeric material. The inner polymeric material can be in the form of a tube. After the metallic ring material is positioned over the inner polymeric material, the outer polymeric material, in the form of a polymeric tube, is positioned over the metallic rings and the inner polymeric material. A shrink tubing 102 is then mounted over the outer polymeric material and then exposed to heat, by a laser 104 to shrink the shrink tubing which in turn applies compressive pressure on the outer polymeric tube. As the outer polymeric tube compresses against the metallic rings and the inner polymeric tube, the heat from the laser causes the inner and outer polymeric materials to melt and fuse together. To facilitate adherence between the inner and outer polymeric materials, an appropriate adhesive or bonding agent 106 can be used in addition to the heat process from the laser. After fusing the inner and outer polymeric materials, the shrink tubing and the mandrel are removed and a laser is used to remove unwanted portions of the polymer to produce the desired stent pattern. For example, as previously described with respect to the stent pattern of FIGS. 4-9, the laser removes portions of the inner and outer polymeric material to form connecting links between the metallic ring material. The resulting stent pattern of rings and links can then be used in conjunction with a stent delivery catheter as shown in FIGS. 1-3 to deliver and implant the stent in a vessel or artery.

In another embodiment, as shown in FIG. 13, in which the metallic ring material 30 is encased or sandwiched between the inner polymeric material 32 and the outer polymeric material 31, a mandrel 100 is first dip coated with the polymer corresponding to the inner polymeric material. The metallic ring material is then positioned on the inner polymeric material which is coating the mandrel. The outer layer of polymeric material is deposited over the metallic ring material and the inner polymeric material either by dip coating or spray coating. Thereafter, the stent having the metallic ring material encased within the inner and outer polymeric materials is removed from the mandrel and by use of a laser or equivalent procedure, the unwanted portions of the polymers are removed to develop the stent pattern.

While the invention has been illustrated and described herein in terms of its use as an intravascular stent, it will be apparent to those skilled in the art that the stent can be used in other body lumens. Further, particular sizes and dimensions, materials used, and the like have been described herein and are provided as examples only. Other modifications and improvements may be made without departing from the scope of the invention.

What is claimed:

1. A stent, comprising:
a metallic body having an undulating stent pattern which includes a plurality of longitudinally spaced apart peaks and a plurality of longitudinally spaced apart valleys aligned along a stent longitudinal axis, wherein a space is formed between each longitudinally spaced apart peak and a space is formed between each longitudinally spaced apart valley;
an outer layer of a polymeric material covering an outer surface of the metallic body; and
an inner layer of a polymeric material covering an inner surface of the metallic body, wherein the inner layer and outer layer of polymeric material are directly joined to one another in the spaces between the longitudinally spaced valleys and longitudinally spaced peaks of the metallic body to form a plurality of polymeric links which extend in the spaces between the longitudinally spaced peaks and longitudinally spaced valleys, the polymeric links being sized and shaped to create areas devoid of any polymeric material in the spaces formed on the stent body.

2. The stent of claim 1, wherein the longitudinally spaced apart peaks of the metallic body are in phase with each other.

3. The stent of claim 1, wherein the longitudinally spaced apart valleys of the metallic body are in phase with each other.

4. The stent of claim 1, wherein the metallic body is formed having a uniform strut width and the polymeric links have a width which is equal to or less than the uniform strut width of the metallic body.

5. The stent of claim 1, wherein the outer layer of a polymeric material is a different material than the inner layer of polymeric material.

6. The stent of claim 1, wherein the outer layer of polymeric material is EVOH.

7. The stent of claim 1, wherein the inner layer of polymeric material is PEEK.

8. The stent of claim 7, wherein the PEEK is radiopaque.

9. The stent of claim 6, wherein the EVOH is radiopaque.

10. The stent of claim 1, wherein the outer layer and inner layer of polymeric materials are taken from the group of polymers consisting of polyetheretherketone (PEEK), ethyl vinyl alcohol (EVOH), polyetherketone, polymethylmethacrylate, polycarbonate, polyphenylenesulfide, polyphenylene, polyvinylfluoride, polyvinylidene fluoride, polypropylene, polyethylene, poly(vinylidene fluoride-co-hexafluoropropylene), poly(ethylene-co-hexafluoropropylene), poly(tetrafluoroethyelene-co-hexafluoropropylene), poly(tetrafluoroethyelene-co-ethylene), polyethyleneterephthalate, polyimides, polyetherimide, ePTFE, polyurethanes, polyetherurethanes, polyesterurethanes, silicone, thermoplastic elastomer, polyether-amide thermoplastic elastomer, fluoroelastomers, fluorosilicone elastomer, styrene-butadiene-styrene rubber, styrene-isoprene-styrene rubber, polybutadiene, polyisoprene, neoprene, ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, butadiene and isoprene and polyester thermoplastic elastomer and a di-block co-polymer of PET and caprolactone.

11. The stent of claim 1, wherein the metallic body is formed of a metal alloy taken from the group of metal alloys consisting of stainless steel, titanium, tantalum, nickel-titanium, cobalt-chromium, and tungsten.

12. The stent of claim 1, wherein one or both of the outer layer or inner layer of polymeric materials are loaded with a therapeutic drug.

13. The stent of claim 12, wherein the therapeutic drug is taken from the group of drugs including one or more of everolimus, rapamycin, actinomycin D (ActD), or derivatives and analogs thereof; synonyms of actinopmycin D including dactinomycin, actinomycin IV, actinomycin I1, actinomycin X1, and actinomycin C1; antiproliferative substances including antineoplastic, antinflammatory, antiplatelet, anticoagulant, antifibrin, antithomobin, antimitotic, antibiotic, antioxidant substances, taxol (paclitaxel and docetaxel), anticoagulants, antifibrins, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein, llb/llla platelet membrane receptor antagonist, recombinant hirudin, thrombin inhibitor methotrexate, azathioprine, vincristine, vinblastine, fluorouracil, adriamycin, mutamycin; angiopeptin, angiotensin converting enzyme inhibitors; calcium channel blockers; colchicine fibroblast growth factor (FGF) antagonists; fish oil (omega 3-fatty acid); histamine antagonist; monoclonal antibodies (such as PDGF receptors); nitroprusside; phosphodiesterase inhibitors; prostaglandin inhibitor (a PDGF antagonist); serotonin blockers; steroids; thioprotease inhibitors; triazolopyrimidine (a PDGF antagonist); and nitric oxide.

14. The stent of claim 1, wherein the stent is configured so that it is visible under any of x-ray fluoroscopy, computer tomography, or MRI.

15. The stent of claim 1, wherein a cavity is formed between the outer layer of polymeric material and the inner layer of polymeric material so that a therapeutic drug can be releasably contained within the cavity.

16. A stent, comprising:
a metallic body having an undulating stent pattern configured so that it is visible under any of x-ray fluoroscopy, computer tomography, or MRI, the stent pattern including a plurality of open spaces which are formed on the metallic body; and
a polymeric material covering an outer surface and inner surface of the metallic body,
wherein a portion of the polymeric material forms polymeric links which extend in the open spaces formed on the metallic body but do not completely cover the open spaces formed on the metallic body to create areas devoid of any polymeric material in the open spaces formed on the stent body.

17. A stent, comprising:
a stent body made from a metallic material, the stent body being configured so that it is visible under any of x-ray fluoroscopy, computer tomography, or MRI, the stent body including areas devoid of any metallic material which create open spaces on the stent body; and
a layer of polymeric material covering an outer surface and inner surface of the stent body; wherein a portion of the polymeric material is formed into a plurality of polymeric links which extend into the open spaces formed on the metallic body, the polymeric links being sized and shaped to create areas devoid of any polymeric material in the open spaces formed on the stent body.

18. A stent, comprising:
a metallic body having an undulating stent pattern which includes a plurality of longitudinally spaced apart peaks and a plurality of longitudinally spaced apart valleys aligned along a stent longitudinal axis, wherein adjacent, longitudinally spaced apart peaks define a space therebetween and adjacent, longitudinally spaced apart valleys define a space therebetween; and
a layer of polymeric material covering an outer surface and inner surface of the metallic body; wherein a plurality of polymeric links are formed from the layer of polymeric material and extend in the spaces formed between adjacent, longitudinally spaced valleys and adjacent, longitudinally spaced peaks of the metallic body, the polymeric links being sized and shaped to create areas devoid of any polymeric material in the spaces formed on the metallic body.

19. A stent, comprising:
a stent body defining a circumferentially extending support structure having an undulating stent pattern which includes a plurality of longitudinally spaced apart peaks and a plurality of longitudinally spaced apart valleys, the plurality of spaced apart peaks and spaced apart valleys being disposed circumferentially on the stent body, wherein adjacent, longitudinally spaced apart peaks define an open space therebetween and adjacent, longitudinally spaced apart valleys define an open space therebetween;
a polymeric material covering an outer surface and inner surface of the metallic body; and
a plurality of polymeric links formed from polymeric material which extend in the spaces formed between adjacent, longitudinally spaced valleys and adjacent, longitudinally spaced peaks of the metallic body, the polymeric links being sized and shaped to create areas devoid of any polymeric material in the spaces formed on the stent body.

20. A stent, comprising:
a stent body made from a metallic material defining a circumferentially extending support structure, the stent body including areas devoid of any metallic material to create open spaces disposed circumferentially along the stent body;
a polymeric material covering an outer surface and an inner surface of the stent body; and
a plurality of polymeric links which extend into the open spaces formed on the stent body, wherein the polymeric links are sized and shaped to create areas devoid of any polymeric material in the open spaces formed on the stent body.

21. The stent of claim 20, wherein the metallic material includes nickel-titanium.

* * * * *